US00PP16522P3

(12) United States Plant Patent
Larsen

(10) Patent No.: US PP16,522 P3
(45) Date of Patent: May 9, 2006

(54) ***OSTEOSPERMUM* PLANT NAMED 'SUNNY AMANDA'**

(50) Latin Name: *Osteospermum ecklonis*
Varietal Denomination: Sunny Amanda

(75) Inventor: Bjarne N. Larsen, Odense (DK)

(73) Assignee: Sunny Gronnegyden APS, Odense (DK)

( * ) Notice: Subject to any disclaimer, the term of this patent is extended or adjusted under 35 U.S.C. 154(b) by 3 days.

(21) Appl. No.: 10/788,297

(22) Filed: Mar. 1, 2004

(65) Prior Publication Data

US 2004/0205873 P1 Oct. 14, 2004

(51) Int. Cl.
*A01H 5/00* (2006.01)

(52) U.S. Cl. ..... Plt./360
(58) Field of Classification Search ..... Plt./360
See application file for complete search history.

(56) References Cited

U.S. PATENT DOCUMENTS

PP12,781 P2 * 7/2002 Kanno ..... Plt./360
2004/0205873 P1 * 10/2004 Larsen ..... Plt./360

OTHER PUBLICATIONS

UPOV ROM GTITM Computer Database, GTI Jouve Retrieval Software 2004/40 Citation for 'Sunny Amanda'.*

* cited by examiner

*Primary Examiner*—Anne Marie Grunberg
*Assistant Examiner*—W. C. Haas
(74) *Attorney, Agent, or Firm*—Foley & Lardner, LLP

(57) ABSTRACT

A new distinct cultivar of *Osteospermum* plant named 'Sunny Amanda', characterized by ray florets with the following mixture of colors: upper surface (when opening): RHS 157D, with a slight yellow tinge at base, gradually changing to RHS 163B at the apex, white to gray-orange; underside (when opening): RHS 162D at base, gradually changing to RHS 161A at the apex with 4 stripes of RHS 177A, gray-orange, (under some light conditions the underside appears golden); upper surfaces (fully opened): RHS 157D, with a slight yellow tinge at base and almost half-way up ray floret, then gradually changing to RHS 163B at the apex, white to gray-orange; underside (fully opened): RHS 162D at base, gradually changing to RHS 161A at the apex with 4 stripes of RHS 153A; disk florets with the following mixture of colors: upper surfaces(when opening): RHS N187D, gray purple; underside (when opening): RHS N155D, white; upper surfaces (fully opened); petal tips are RHS N187, purple; underside (fully opened): RHS N155D, white; dense and bushy plant form; with globular plant habit; moderately vigorous growth habit, but less need for chemical growth retardation, and obovate to lanceolate leaves.

3 Drawing Sheets

Botanical designation: *Osteospermum ecklonis.*
Variety denomination: 'Sunny Amanda'.

BACKGROUND OF THE INVENTION

The present Invention relates to a new and distinct cultivar of *Osteospermum* plant, botanically known as *Osteospermum ecklonis,* commonly known by the name Cape Daisy, and hereinafter referred to by the name 'Sunny Amanda'.

The new *Osteospermum* is a product of a planned breeding program conducted by the Inventor, Bjarne Larsen, in Stige, Denmark. The new *Osteospermum* originated from a cross made in 2000 by the Inventor between *Osteospermum ecklonis,* variety name 'Sunny Alex' (unpatented) and *Osteospermum ecklonis* cultivar designated '998' (unpatented). The Inventor discovered and selected the new *Osteospermum* cultivar as a single flowering plant from the progeny of the above crossing in 2002 on the basis of its inflorescence color and compact, freely branching habit. Plants of the new *Osteospermum* are upright, compact and have a unique color combination of upper and underside of the ray florets.

Asexual reproduction of the new cultivar by terminal vegetative cuttings taken and propagated during trial production batches in Stige, Denmark, has shown that the unique features of this new *Osteospermum* are stable and reproduced true to type in many successive generations.

BRIEF SUMMARY OF THE INVENTION

Plants of the cultivar 'Sunny Amanda' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'Sunny Amanda'. These characteristics in combination distinguish 'Sunny Amanda' as a new and distinct cultivar:

1. Ray florets with the following mixture of colors: upper surface (when opening): RHS 157D, with a slight yellow tinge at base, gradually changing to RHS 163B at the apex, white to gray-orange; underside (when opening): RHS 162D at base, gradually changing to RHS 161A at the apex with 4 stripes of RHS 177A, gray-orange, (under some light conditions the underside appears golden); upper surfaces (fully opened): RHS 157D, with a slight yellow tinge at base and almost half-way up ray floret, then gradually changing to RHS 163B at the apex, white to gray-orange; underside (fully opened): RHS 162D at base, gradually changing to RHS 161A at the apex with 4 stripes of RHS 153A.

2. Disk florets with the following mixture of colors: upper surfaces(when opening): RHS N187D, gray purple; underside (when opening): RHS N155D, white; upper surfaces (fully opened): Petal tips are RHS N187, purple; underside (fully opened): RHS N155D, white.
3. Dense and bushy plant form; with globular plant habit.
4. Moderately vigorous growth habit, but less need than is typical of the species for chemical growth retardation.
5. Obovate to lanceolate leaves.

Plants of the cultivar 'Sunny Amanda' can be compared to plants of the *Osteospermum ecklonis* parental cultivar 'Sunny Alex' (unpatented). In side-by-side comparisons conducted by the Inventor in Stige, Denmark, plants of the cultivar 'Sunny Amanda' and the cultivar 'Sunny Alex' differ in the following characteristics:

1. 'Sunny Amanda' has striking color combinations of white ray florets with yellow tinge at the apex RHS 163B, and gray-purple disk with orange pollen, while 'Sunny Alex' is orange yellow.
2. 'Sunny Amanda' has entire, obovate to lanceolate leaves while the leaves of 'Sunny Alex' are broadly lobed.
3. 'Sunny Amanda' has longer, but sturdier peduncles than plants of the cultivar 'Sunny Alex'.
4. 'Sunny Amanda' is globular and more compact than the upright plants of the cultivar 'Sunny Alex'.
5. 'Sunny Amanda' has fewer and larger inflorescences per plant than the plants of the cultivar 'Sunny Alex'.

Plants of the cultivar 'Sunny Amanda' are most similar to plants of the parental cultivar *Osteospermum ecklonis* 'Sunny Alex' as described above.

BRIEF DESCRIPTION OF THE PHOTOGRAPHS

The accompanying colored photographs illustrate the overall appearance of the new *Osteospermum* cultivar 'Sunny Amanda' showing the colors as true as is reasonably possible with colored reproductions of this type. Colors in the photographs may differ slightly from the color values cited in the detailed botanical description which accurately describe the color of the new *Osteospermum* cultivar 'Sunny Amanda'.

The first photograph is a top view of a typical flowering plant of 'Sunny Amanda' as grown in an 11 cm pot.

The second photograph is a close-up of the composite inflorescence of 'Sunny Amanda'.

The third photograph shows the inflorescences and leaves of 'Sunny Amanda' (in the third photograph, 'Sunny Amanda' is labelled by its breeder's reference no. '30.013.01').

DETAILED BOTANICAL DESCRIPTION

The aforementioned photographs, together with the following observations, measurements and values describe the new *Osteospermum* cultivar as grown in a glass, greenhouse in Stige, Denmark, under conditions which closely approximate those generally used in commercial practice. The plants were grown in a greenhouse when the average daytime temperature in the greenhouse was 14° C. and the average night time temperature in the greenhouse was 12° C. The cultivar was grown under natural light conditions with 35 W/m2 supplementary light when natural light conditions was less than 40 W/m$^2$. The peat based soil mix was watered with a solution of Pioneer Macro 10-4-25 in a 200 ppm N-P-K solution giving a conductivity of 2.5 m$^2$. Chlormequat 3×0.5% drench was used as a growth retardant. The cultivar was produced in a 11 cm pot, and the reaction time from day of induction to day of first opened inflorescence is about 3 weeks.

In the following description, color references are made to The Royal Horticultural Society Colour Chart, 4$^{th}$ edition, except where general color terms of ordinary dictionary significance are used. Color values were taken under daylight conditions at approximately 10:00 a.m. Plants used for this description were grown for about 20 weeks after cutting.

Botanical classification: *Osteospermum ecklonis.*

Parentage:

*Female parent.*—*Osteospermum ecklonis* variety name 'Sunny Alex' (unpatented).

*Male parent.*—*Osteospermum ecklonis* cultivar designated '998' (unpatented).

Plant description:

*Form.*—Perennial plant with globular plant habit. *Osteospermum* inflorescences in composite heads. Freely branching with lateral flowering branches forming at every node; dense and bushy.

*Crop time.*—After rooting, about 20 weeks are required to produce finished flowering plants in 11 cm pots.

*Plant height* (*soil level to top of plant plane*).—About 20 cm.

*Plant spread* (*diameter*).—Typical: 21 cm. Observed: 20 to 22 cm.

*Vigor.*—Moderately vigorous growth rate.

*Propagation.*—Type cutting: terminal vegetative cuttings.

*Time to initiate roots.*—About 10 to 14 days at 18° C. to 21° C. in tunnels in a greenhouse.

*Root description.*—Fine, well branched.

*Root color.*—White, RHS 155C (washed roots).

Branches description: Number of branches per plant: 4 primary and 7 secondary (flowering). Length: Primary: About 3 cm. Secondary: 12 cm to 14 cm. Diameter: 4 cm to 5 cm. Internode length: About 3 mm. Strength/Shape: Sturdy, round cross-section. Aspect: Upright then bending outwardly at 70 degree angle. Texture: Smooth, glabrous. Color: (upper and lower surfaces): Yellow-green, RHS 144C.

Foliage description: Leaves alternate, single, slightly lobed, pinnate venation. Length: 3 cm to 5 cm. Width: About 30 mm. Shape: Obovate to lanceolate. Apex: obtuse. Base: attenuate. Margin: broadly dentate. Texture: smooth, glabrous, shiny. Scattered short, stiff hairs. Color: Young foliage, upper surfaces RHS 147A, yellow-green and lower surface RHS 148C. Mature foliage, upper surface RHS 139B, yellow-green and lower surface RHS 147A. Venation pattern: Pinnate. Venation color: RHS 148B. Petiole length: 5 mm to 10 mm. Petiole diameter: 2 mm to 4 mm. Petiole texture: (upper and lower surfaces): smooth. Petiole color: (upper surface and lower surfaces): Yellow-green, RHS 145B.

Inflorescence description:

*Inflorescence arrangement and shape.*—Tubular disk and flat lanceolate ray florets in single, composite daisy capitulae; with 15 parted involucre. 10 cm sturdy peduncles.

*Natural flowering season.*—Continuous throughout the spring and summer in temperate regions. Season can be extended by vernalization and long day treatments.

*Flower longevity on the plant.*—5 to 9 days; longevity of individual inflorescences is highly dependent on temperature and light conditions. Inflorescences not self-cleaning.

*Fragrance.*—Weak, fresh lemon fragrance.

*Inflorescence diameter.*—About 7 cm.

*Inflorescence depth.*—Typical: 5 mm to 8 mm. Observed: About 6 mm.

*Quantity of inflorescences per lateral stem.*—About 2.

*Quantity of inflorescence buds per lateral stem.*—About 8.

*Quantity of inflorescences and buds per plant.*—About 25 to 30.

Bud:

*Length.*—Up to 12 mm when showing color. Diameter: Up to 10 mm. Shape: Globular until showing color. Rate of opening: 3 per plant per week. Color: From RHS 145C at base to RHS 146B.

Inflorescences:

Ray florets:

*Ray florets.*—Typical number of ray florets per inflorescence: 15. Observed number of ray florets per inflorescence: 13 to 17. Length: Ray florets: About 27 mm. Width (diameter): About 8 mm. Shape: Lanceolate to elliptic, with an acute tip. Ray floret base: Fused. Ray floret margin: entire. Ray floret color: Upper surfaces (when opening): RHS 157D, with a slight yellow tinge at base, gradually changing to RHS 163B at the apex, white to gray-orange; underside (when opening): RHS 162D at base, gradually changing to RHS 161A at the apex with 4 stripes of RHS 177A, gray-orange; (under some light conditions the underside appears golden). Upper surfaces (fully opened): RHS 157D, with a slight yellow tinge at base and almost half-way up ray floret, then gradually changing to RHS 163B at the apex, white to gray-orange; underside (fully opened): RHS 162D at base, gradually changing to RHS 161A at the apex with 4 stripes of RHS 153A.

Disk florets: Typical number of disks florets per inflorescence: 75. Observed number of disks florets per inflorescence: 60 to 85, fused at base. Length: Disk florets: About 5 mm. Width (diameter): About 2 mm. Disk floret overall shape: tubular. Disk floret apex: Attenuate. Disk floret base: Fused. Disk floret margin: entire. Disk florets color: Upper surfaces (when opening): RHS N187D, gray purple; underside (when opening): RHS N155D, white. Upper surfaces (fully opened): Petal tips are RHS N187, purple; underside (fully opened): RHS N155D, white.

Phyllary: Observed number of phyllaries: 12 to 15. Typical number of phyllaries: 13. Length: 6 mm to 12 mm. Width: 1 mm to 3 mm. Overall shape: Lanceolate. Apex shape: Acuminate. Base shape: Fused. Margin: Entire. Color: Upper surface: RHS 137B; lower surface: RHS 137D, green.

Peduncle: Strength: strong. Length: About 10 cm. Diameter: About 2 mm. Color: RHS 144C, yellow-green.

Reproductive organs:

*Androecium.*—Location: Disc florets only.

*Stamen/anthers.*—Typical number: 5. Observed number: 5. Linear fused, color RHS 202A, black. Anther size: 2 mm.

*Pollen.*—Typical Amount: Plenty. Observed Amount: Plenty. Color RHS N25A, orange.

*Gynoecium.*—Location: Ray and disc florets.

*Pistil and stigma.*—Typical number: 1. Observed number: 1. Length: 4 mm. Diameter: 4 mm. Stigma shape: brushlike. Stigma color RHS N187B, purple.

*Style.*—Length: 2 mm.

*Ovary.*—Color: RHS 2D, green-yellow.

*Seed.*—Length: About 1 mm. Diameter: About 0.3 mm. Seed is sterile.

Disease/pest resistance: Good.

Disease/pest susceptibility: Low.

Weather tolerance: Plants of the new *Osteospermum* have exhibited good tolerance to drought, rain and wind, however flowering may cease during hot periods above 30° C.

I claim:

1. A new and distinct cultivar of *Osteospermum* plant named 'Sunny Amanda', as illustrated and described herein.

* * * * *

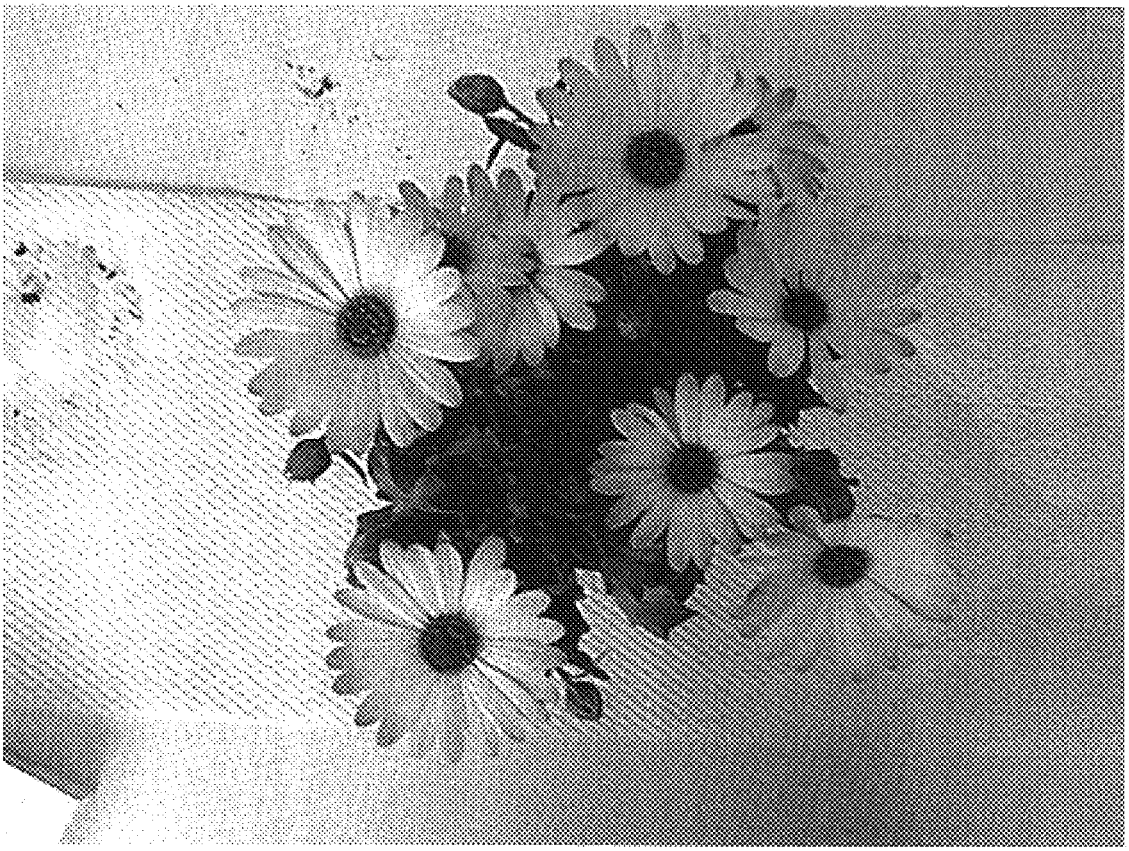

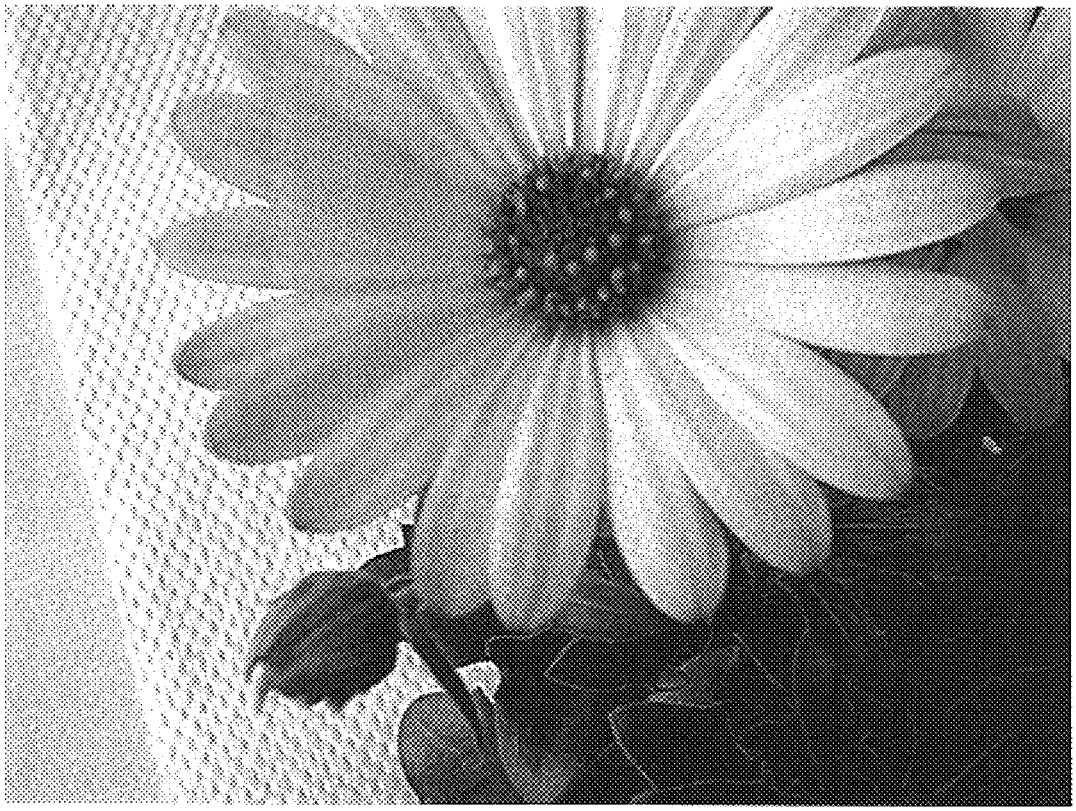

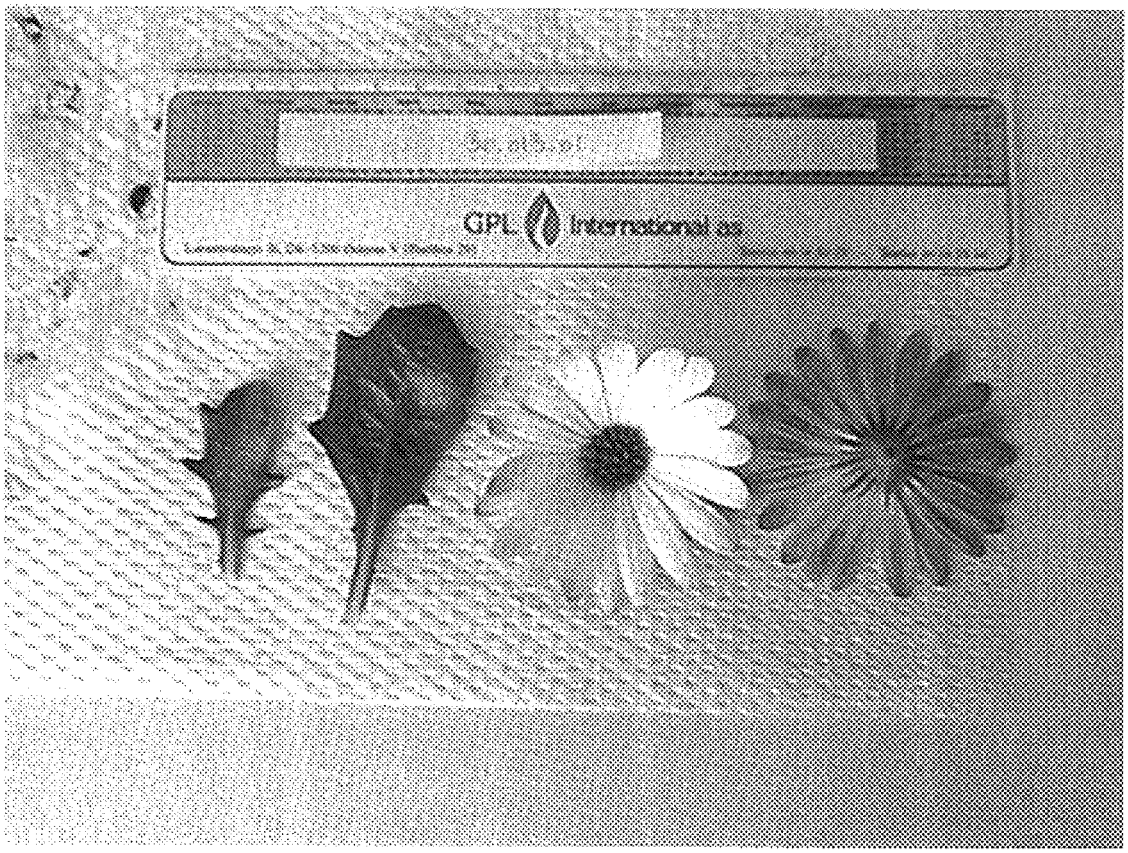
GPL International ag